(12) United States Patent
Marks et al.

(10) Patent No.: US 9,526,505 B2
(45) Date of Patent: Dec. 27, 2016

(54) INTRACORPOREAL OCCLUSIVE DEVICE AND METHOD

(75) Inventors: Michael P. Marks, Hillsborough, CA (US); Michael Ross, Hillsborough, CA (US)

(73) Assignee: MicroVention, Inc., Tustin, CA (US)

( * ) Notice: Subject to any disclaimer, the term of this patent is extended or adjusted under 35 U.S.C. 154(b) by 1105 days.

(21) Appl. No.: 12/275,126

(22) Filed: Nov. 20, 2008

(65) Prior Publication Data

US 2009/0076540 A1 Mar. 19, 2009

Related U.S. Application Data

(60) Continuation of application No. 11/418,551, filed on May 3, 2006, now Pat. No. 8,932,317, which is a
(Continued)

(51) Int. Cl.
*A61M 29/00* (2006.01)
*A61B 17/12* (2006.01)
(Continued)

(52) U.S. Cl.
CPC ..... *A61B 17/12113* (2013.01); *A61B 17/1214* (2013.01); *A61B 17/12022* (2013.01); *A61B 17/12109* (2013.01); *A61B 17/12136* (2013.01); *A61B 17/12145* (2013.01); *A61B 17/12163* (2013.01); *A61B 17/12195* (2013.01); *A61B 2017/00477* (2013.01);
(Continued)

(58) Field of Classification Search
CPC .............. A61B 17/12022; A61B 17/12109; A61B 17/12113; A61B 17/1214; A61B 2017/1205; A61B 2017/12054; A61B 2017/12059; A61B 2017/12068; A61B 2017/1209

USPC ............ 606/200, 108, 191, 192, 198
See application file for complete search history.

(56) References Cited

U.S. PATENT DOCUMENTS 4,346,712 A 8/1982 Handa et al.
4,364,392 A 12/1982 Strother et al.
(Continued)

FOREIGN PATENT DOCUMENTS

EP 0547530 A1 6/1993
EP 0707830 A1 4/1996
(Continued)

OTHER PUBLICATIONS

European Search Report (European Patent Application No. EP 07 11 7926); Jan. 28, 2008, 10 pages.
(Continued)

*Primary Examiner* — Katherine Rodjom
(74) *Attorney, Agent, or Firm* — Inskeep IP Group, Inc.

(57) ABSTRACT

An intracorporeal space filling device and a delivery system and method for using the device is disclosed. The space filling device is preferably configured for percutaneous delivery from a peripheral conduit of a patient. The space filling device has an elongated tubular or interconnected bead structure which may have a transmutable material disposed within it. The transmutable material can be altered from a non-rigid state to a rigid state by the application of various types of energy or by other suitable means. The space filling device can be positioned by a delivery system and detached from the delivery system after desired positioning is achieved.

13 Claims, 10 Drawing Sheets

Related U.S. Application Data continuation of application No. 11/169,322, filed on Jun. 28, 2005, now abandoned, which is a continuation of application No. 11/033,463, filed on Jan. 11, 2005, now abandoned, which is a continuation of application No. 10/106,511, filed on Mar. 25, 2002, now abandoned, which is a division of application No. 09/324,987, filed on Jun. 2, 1999, now abandoned.

(51) Int. Cl.
  *A61B 17/00* (2006.01)
  *A61B 17/22* (2006.01)
  *A61M 25/10* (2013.01)

(52) U.S. Cl.
  CPC ............ *A61B 2017/00867* (2013.01); *A61B 2017/12063* (2013.01); *A61B 2017/12068* (2013.01); *A61B 2017/12072* (2013.01); *A61B 2017/12077* (2013.01); *A61B 2017/22068* (2013.01); *A61B 2017/22069* (2013.01); *A61M 2025/1052* (2013.01)

(56) References Cited

U.S. PATENT DOCUMENTS

| | | |
|---|---|---|
| 4,402,319 A | 9/1983 | Handa et al. |
| 4,512,338 A | 4/1985 | Balko et al. |
| 4,545,367 A | 10/1985 | Tucci |
| 4,551,132 A | 11/1985 | Pásztor et al. |
| 4,638,803 A | 1/1987 | Rand |
| RE32,348 E | 2/1987 | Pevsner |
| 4,735,201 A | 4/1988 | O'Reilly |
| 4,795,741 A | 1/1989 | Leshchiner et al. |
| 4,819,637 A | 4/1989 | Dormandy, Jr. et al. |
| 4,944,746 A | 7/1990 | Iwata et al. |
| 4,994,069 A | 2/1991 | Ritchart et al. |
| 5,108,407 A | 4/1992 | Geremia et al. |
| 5,122,136 A | 6/1992 | Guglielmi et al. |
| 5,133,731 A | 7/1992 | Butler et al. |
| 5,163,952 A | 11/1992 | Froix |
| 5,217,484 A | 6/1993 | Marks |
| 5,226,911 A | 7/1993 | Chee et al. |
| 5,250,071 A | 10/1993 | Palermo |
| 5,256,146 A | 10/1993 | Ensminger et al. |
| 5,258,042 A | 11/1993 | Mehta |
| 5,304,194 A | 4/1994 | Chee et al. |
| 5,312,415 A | 5/1994 | Palermo |
| 5,334,201 A | 8/1994 | Cowan |
| 5,334,210 A | 8/1994 | Gianturco |
| 5,350,397 A | 9/1994 | Palermo et al. |
| 5,354,295 A | 10/1994 | Guglielmi et al. |
| 5,382,259 A | 1/1995 | Phelps et al. |
| 5,382,260 A | 1/1995 | Dormandy, Jr. et al. |
| 5,423,777 A | 6/1995 | Tajiri et al. |
| 5,423,829 A | 6/1995 | Pham et al. |
| 5,423,849 A | 6/1995 | Engelson et al. |
| 5,443,454 A | 8/1995 | Tanabe et al. |
| 5,443,478 A | 8/1995 | Purdy |
| 5,443,495 A | 8/1995 | Buscemi et al. |
| 5,469,867 A | 11/1995 | Schmitt |
| 5,476,472 A | 12/1995 | Dormandy, Jr. et al. |
| 5,498,227 A | 3/1996 | Mawad |
| 5,522,836 A | 6/1996 | Palermo |
| 5,525,334 A | 6/1996 | Ito et al. |
| 5,529,653 A | 6/1996 | Glastra |
| 5,536,274 A | 7/1996 | Neuss |
| 5,569,245 A | 10/1996 | Guglielmi et al. |
| 5,578,074 A | 11/1996 | Mirigian |
| 5,580,568 A | 12/1996 | Greff et al. |
| 5,582,619 A | 12/1996 | Ken |
| 5,601,600 A | 2/1997 | Ton |
| 5,612,050 A | 3/1997 | Rowe et al. |
| 5,614,204 A | 3/1997 | Cochrum |
| 5,624,449 A | 4/1997 | Pham et al. |
| 5,624,461 A | 4/1997 | Mariant |
| 5,624,685 A | 4/1997 | Takahashi et al. |
| 5,634,936 A | 6/1997 | Linden et al. |
| 5,639,277 A | 6/1997 | Mariant et al. |
| 5,645,558 A | 7/1997 | Horton |
| 5,658,308 A | 8/1997 | Snyder |
| 5,667,767 A | 9/1997 | Greff et al. |
| 5,669,931 A | 9/1997 | Kupiecki et al. |
| 5,690,667 A | 11/1997 | Gia |
| 5,690,671 A | 11/1997 | McGurk et al. |
| 5,700,258 A | 12/1997 | Mirigian et al. |
| 5,702,361 A | 12/1997 | Evans et al. |
| 5,718,711 A | 2/1998 | Berenstein et al. |
| 5,722,989 A | 3/1998 | Fitch et al. |
| 5,725,568 A | 3/1998 | Hastings |
| 5,733,329 A | 3/1998 | Wallace et al. |
| 5,743,905 A | 4/1998 | Eder et al. |
| 5,749,891 A | 5/1998 | Ken et al. |
| 5,749,894 A | 5/1998 | Engelson |
| 5,759,161 A | 6/1998 | Ogawa et al. |
| 5,766,204 A | 6/1998 | Porter et al. |
| 5,766,219 A | 6/1998 | Horton |
| 5,792,154 A | 8/1998 | Doan et al. |
| 5,800,454 A | 9/1998 | Jacobsen et al. |
| 5,800,455 A | 9/1998 | Palermo et al. |
| 5,814,062 A | 9/1998 | Sepetka et al. |
| 5,823,198 A | 10/1998 | Jones et al. |
| 5,830,178 A | 11/1998 | Jones et al. |
| 5,830,230 A | 11/1998 | Berryman et al. |
| 5,846,210 A | 12/1998 | Ogawa et al. |
| 5,846,247 A * | 12/1998 | Unsworth et al. ............ 606/108 |
| 5,851,206 A * | 12/1998 | Guglielmi et al. ............ 606/28 |
| 5,851,508 A | 12/1998 | Greff et al. |
| 5,891,058 A | 4/1999 | Taki et al. |
| 5,902,254 A | 5/1999 | Magram |
| 5,911,737 A | 6/1999 | Lee et al. |
| 5,941,888 A | 8/1999 | Wallace et al. |
| 5,944,733 A | 8/1999 | Engelson |
| 5,947,963 A | 9/1999 | Guglielmi |
| 5,964,797 A | 10/1999 | Ho |
| 5,976,131 A | 11/1999 | Guglielmi et al. |
| 5,984,629 A | 11/1999 | Brodersen et al. |
| 5,984,929 A | 11/1999 | Bashiri et al. |
| 6,013,084 A | 1/2000 | Ken et al. |
| 6,015,424 A | 1/2000 | Rosenbluth et al. |
| 6,033,423 A | 3/2000 | Ken et al. |
| 6,059,815 A | 5/2000 | Lee et al. |
| 6,086,599 A | 7/2000 | Lee et al. |
| 6,159,206 A | 12/2000 | Ogawa |
| 6,221,066 B1 | 4/2001 | Ferrera et al. |
| 6,238,403 B1 | 5/2001 | Greene, Jr. et al. |
| 6,277,126 B1 | 8/2001 | Barry et al. |
| 6,293,960 B1 | 9/2001 | Ken |
| 6,296,622 B1 | 10/2001 | Kurz et al. |
| 6,299,619 B1 | 10/2001 | Greene, Jr. et al. |
| 6,371,979 B1 | 4/2002 | Beyar et al. |
| 6,375,668 B1 | 4/2002 | Gifford et al. |
| 6,375,669 B1 | 4/2002 | Rosenbluth et al. |
| 6,383,204 B1 | 5/2002 | Ferrera et al. |
| 6,425,893 B1 | 7/2002 | Guglielmi |
| 6,526,979 B1 | 3/2003 | Nikolchev et al. |
| 6,602,269 B2 | 8/2003 | Wallace et al. |
| 6,610,046 B1 | 8/2003 | Usami et al. |
| 6,634,361 B1 | 10/2003 | Nikolchev et al. |
| 6,656,173 B1 | 12/2003 | Palermo |
| 6,684,884 B2 | 2/2004 | Nikolchev et al. |
| 6,705,323 B1 | 3/2004 | Nikolchev et al. |
| 6,743,236 B2 | 6/2004 | Barry et al. |
| 2002/0107534 A1 | 8/2002 | Schaefer et al. |
| 2006/0253149 A1 | 11/2006 | Gandhi et al. |

FOREIGN PATENT DOCUMENTS

| | | |
|---|---|---|
| EP | 07078301 A1 | 4/1996 |
| EP | 0719522 A1 | 7/1996 |
| EP | 0948935 A1 | 10/1999 |
| EP | 1073377 | 2/2001 |
| EP | 0824010 B1 | 2/2003 |

(56) References Cited

FOREIGN PATENT DOCUMENTS

| | | | |
|---|---|---|---|
| EP | 0830873 | B1 | 4/2004 |
| EP | 1073377 | B1 | 11/2004 |
| JP | 56-43962 | A | 4/1981 |
| JP | 01-238874 | | 9/1989 |
| JP | 01-238874 | A | 9/1989 |
| JP | 07-265431 | A | 10/1995 |
| JP | 08-50633 | A | 7/1996 |
| JP | 08-506033 | A | 7/1996 |
| JP | 10-94542 | A | 4/1998 |
| WO | WO91/13592 | A1 | 9/1991 |
| WO | WO 91/13592 | A1 | 9/1991 |
| WO | WO 94/06503 | A1 | 3/1994 |
| WO | WO94/06503 | A1 | 3/1994 |
| WO | WO94/10936 | A1 | 5/1994 |
| WO | WO 94/10936 | A1 | 5/1994 |
| WO | WO95/07667 | A1 | 3/1995 |
| WO | WO 95/07667 | A1 | 3/1995 |
| WO | WO95/27443 | A1 | 10/1995 |
| WO | WO 95/27443 | A1 | 10/1995 |
| WO | WO96/00034 | A1 | 1/1996 |
| WO | WO 96/00034 | A1 | 1/1996 |
| WO | WO 96/00104 | A1 | 1/1996 |
| WO | WO96/00104 | A1 | 1/1996 |
| WO | WO97/26939 | A1 | 7/1997 |
| WO | WO 97/26939 | A1 | 7/1997 |
| WO | WO 97/27888 | A1 | 8/1997 |
| WO | WO97/27888 | A1 | 8/1997 |
| WO | WO98/29042 | A1 | 7/1998 |
| WO | WO 98/29042 | A1 | 7/1998 |
| WO | WO 98/37816 | A1 | 9/1998 |
| WO | WO98/37816 | A1 | 9/1998 |
| WO | WO98/40033 | A2 | 9/1998 |
| WO | WO 98/40033 | A3 | 9/1998 |
| WO | WO 99/02094 | A1 | 1/1999 |
| WO | WO99/09894 | A1 | 3/1999 |
| WO | WO 99/09894 | A1 | 3/1999 |
| WO | WO 99/29260 | A2 | 6/1999 |
| WO | WO99/29260 | A2 | 6/1999 |
| WO | WO 99/40852 | A1 | 8/1999 |
| WO | WO99/40852 | A1 | 8/1999 |
| WO | WO99/42059 | A2 | 8/1999 |
| WO | WO 99/42059 | A2 | 8/1999 |
| WO | WO 99/55239 | A1 | 11/1999 |
| WO | WO99/55239 | A1 | 11/1999 |
| WO | WO 00/12031 | A1 | 3/2000 |
| WO | WO00/12031 | A1 | 3/2000 |
| WO | WO 00/53105 | A1 | 9/2000 |
| WO | WO00/53105 | A1 | 9/2000 |
| WO | WO 00/72781 | A2 | 12/2000 |
| WO | WO00/72781 | A2 | 12/2000 |
| WO | WO01/58366 | A1 | 8/2001 |
| WO | WO 01/58366 | A1 | 8/2001 |

OTHER PUBLICATIONS

European Search Report (European Patent Application No. EP 07 11 7926); Nov. 7, 2007, 5 pages.

European Search Report (European Patent Application No. EP 00 93 6492; May 27, 2003.

PCT Search Report for PCT/US00/15445 dated Sep. 11, 2000, Applicant: Sethel Interventional, Inc.

Schmutz, F. et al., "Embolization of Cerebral Arteriovenous Malformations with Silk: Histophathologic Changes and Hemorrhagic Complications," *AJNR AM J M Neuroradial* (Aug. 1997 vol. 18, pp. 1233-1237.

Graves, V.B. et al., "Endovascular Occlusion of the Carotid or Vertebral Artery with Temporary Proximal Flow Arrest and Microcoils: Clinical Results," *AJNR AM J Neuroradial* (Aug. 1997) vol. 18, pp. 1201-1206.

Vinuela, F. et al., "Guglielmi detachable coil embolization of acute intracranial aneurysm; perioperative anatomical and clinical outcome in 403 patients," *J Neurosur* (Mar. 1997) vol. 86, pp. 475-482.

Higashida, R.T, M.D. et al., "Interventional Treatment of Intracranial Aneurysms," pp. 460-463, 1995, *Cerebrovascular Disease: Imaging and Interventional Treatment Options*. Ed: Rumbaugh CL, Wang A, Tsai FY, Igaku-Shoin, New York, Tokyo.

European Patent Office, in European Patent Application No. 08163004.8-2319/1992308, Office Action dated Jun. 25, 2010, 7 pages.

European Patent Office, in European Patent Application No. 08163004.8-2319/1992308, Search Report dated Nov. 3, 2009, 6 pages.

European Patent Office, in European Patent Application No. 00 936 492.8-2305, Office Action dated Jul. 2, 2004, 3 pages.

European Patent Office, in European Patent Application No. 00 936 492.8-2305, Office Action dated Nov. 11, 2003, 3 pages.

United States Patent and Trademark Office, Office Action mailed Mar. 22, 2011 in U.S. Appl. No. 11/418,551, 12 pages.

European Patent Office, Examination Report dated Jun. 25, 2010 in European Patent Application No. 08163004.8-2319, 7 pages.

European Patent Office, Supplementary European Search Report dated Nov. 3, 2009 in European Patent Application No. 08163004.8-2319, 6 pages.

United States Patent and Trademark Office, Final Office Action mailed Aug. 20, 2009 in U.S. Appl. No. 11/418,551, 7 pages.

United States Patent and Trademark Office, Office Action mailed Oct. 28, 2008 in U.S. Appl. No. 11/418,488, 6 pages.

United States Patent and Trademark Office, Office Action mailed Oct. 6, 2008 in U.S. Appl. No. 11/418,551, 15 pages.

European Patent Office, Supplementary European Search Report dated Jan. 28, 2008 in European Patent Application No. 07117926.1-1265, 10 pages.

European Patent Office, Supplementary European Search Report dated Nov. 7, 2007 in European Patent Application No. 07117926.1-1265, 5 pages.

United States Patent and Trademark Office, Office Action mailed Mar. 26, 2007 in U.S. Appl. No. 11/033,463, 5 pages.

United States Patent and Trademark Office, Office Action mailed Feb. 6, 2007 in U.S. Appl. No. 11/169,322, 6 pages.

United States Patent and Trademark Office, Office Action mailed Aug. 11, 2004 in U.S. Appl. No. 10/106,511, 10 pages.

European Patent Office, Examination Report dated Jul. 2, 2004 in European Patent Application No. 00936492.8-2305, 3 pages.

European Patent Office, Examination Report dated Nov. 11, 2003 in European Patent Application No. 00936492.8-2305, 3 pages.

European Patent Office, Supplementary European Search Report dated May 27, 2003 in European Patent Application No. 00936492.8, 3 pages.

WIPO, European International Search Authority, International Search Report dated Nov. 27, 2000 in International Patent Application No. PCT/US00/15445, 6 pages.

United States Patent and Trademark Office, Office Action mailed Mar. 30, 2000 in U.S. Appl. No. 09/324,987, 17 pages.

Schmutz, F. et al., "Embolization of Cerebral Arteriovenous Malformations with Silk: Histophathologic Changes and Hemorrhagic Complications," *AJNR Am J Neuroradiol* 18: 1233-1237, Aug. 1997, 5 pages.

Graves, V.B. et al., "Endovascular Occlusion of the Carotid or Vertebral Artery with Temporary Proximal Flow Arrest and Microcoils: Clinical Results," *AJNR Am J Neuroradiol* 18:1201-1206, Aug. 1997, 6 pages.

Viñuela, F. et al., "Guglielmi detachable coil embolization of acute intracranial aneurysm: perioperative anatomical and clinical outcome in 403 patients," *J Neurosurg* 86:475-486, Mar. 1997, 8 pages.

\* cited by examiner

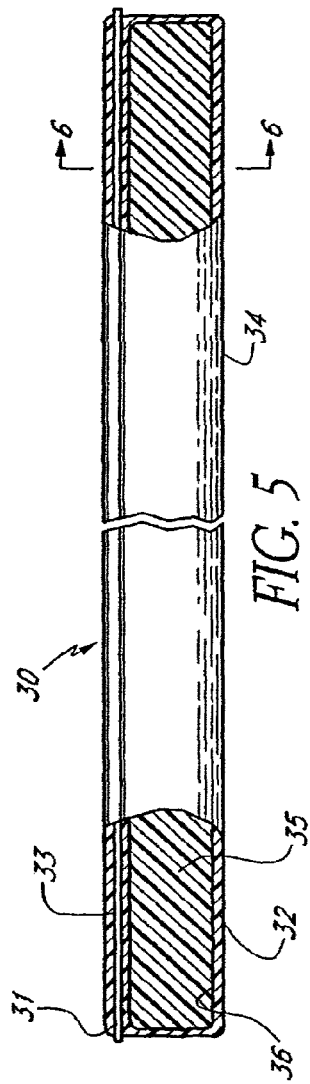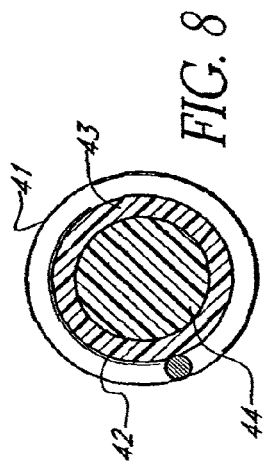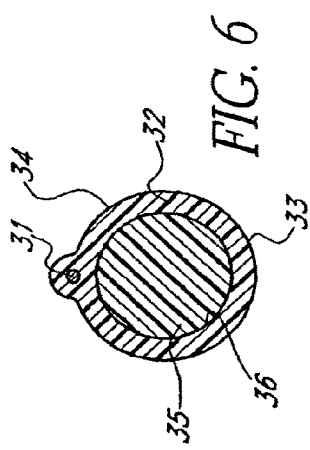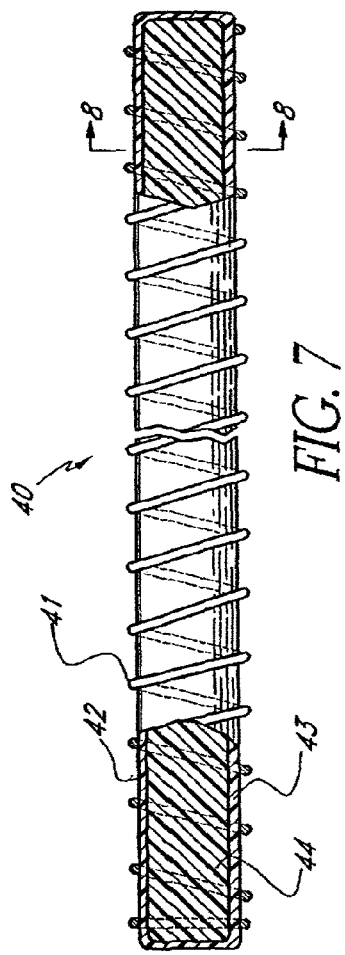

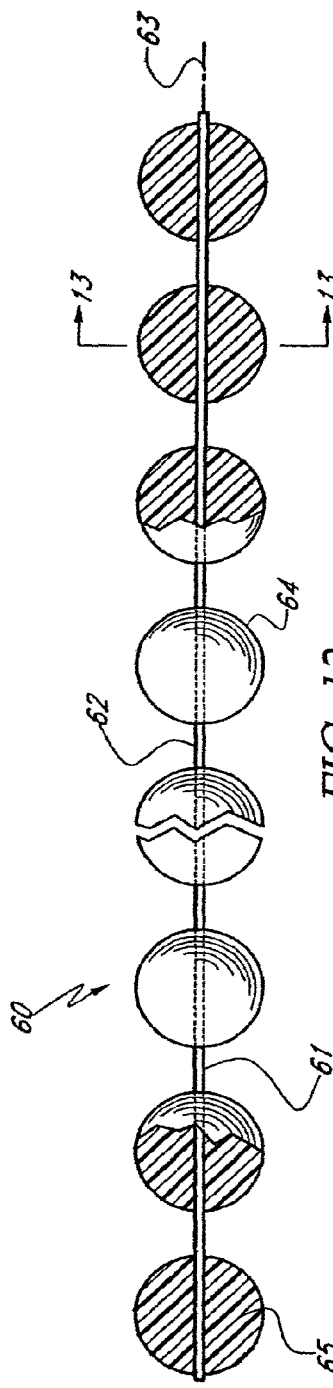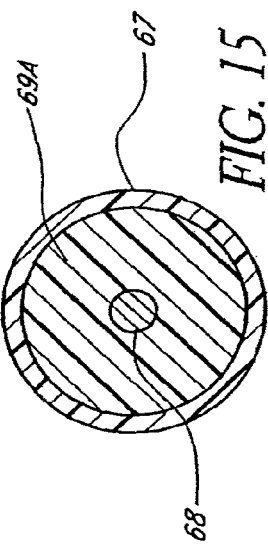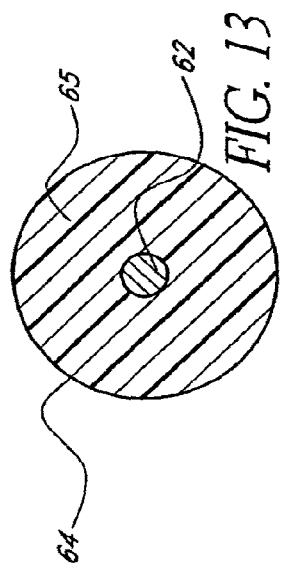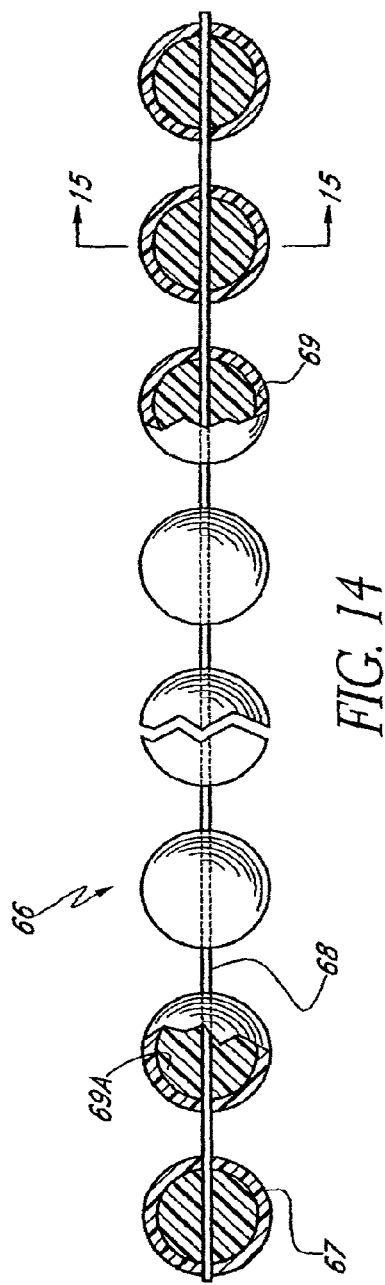

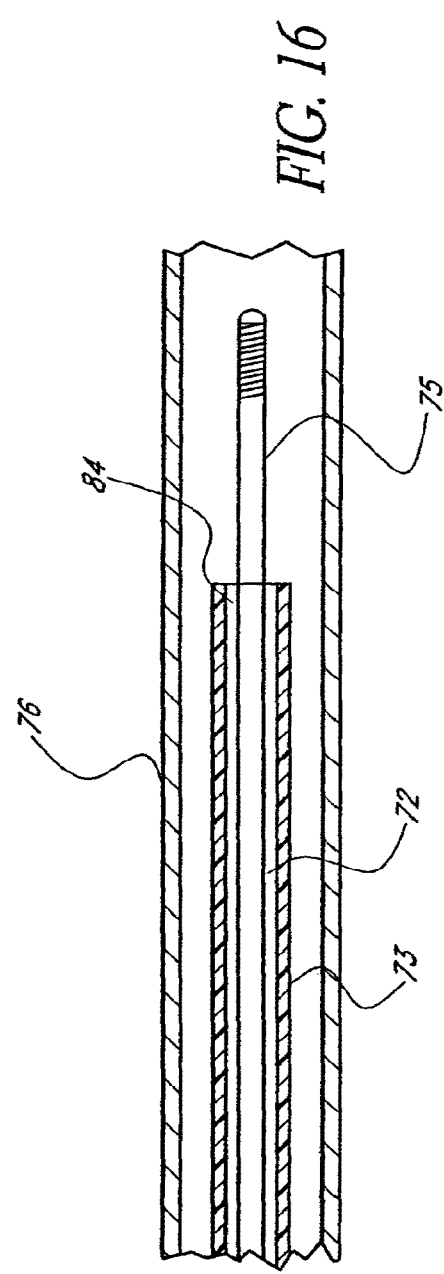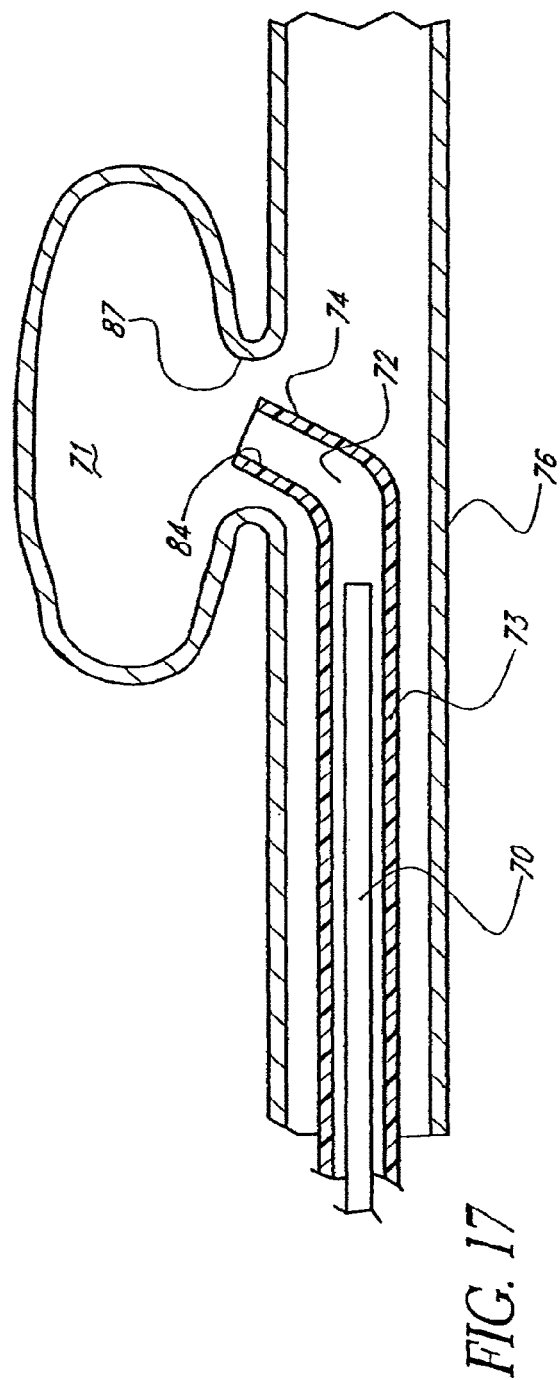

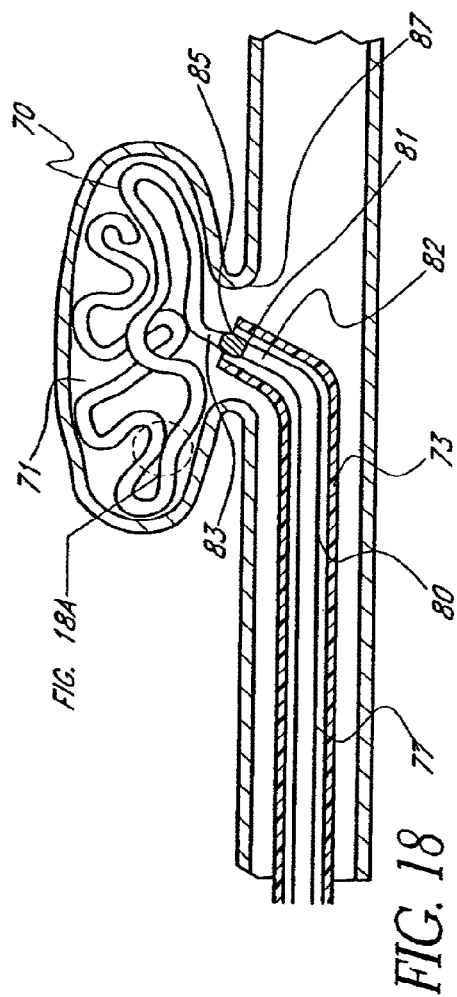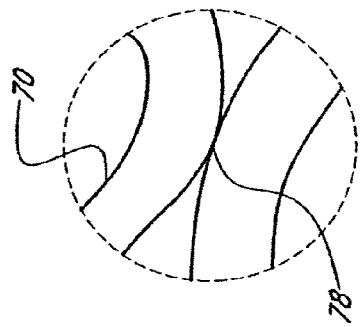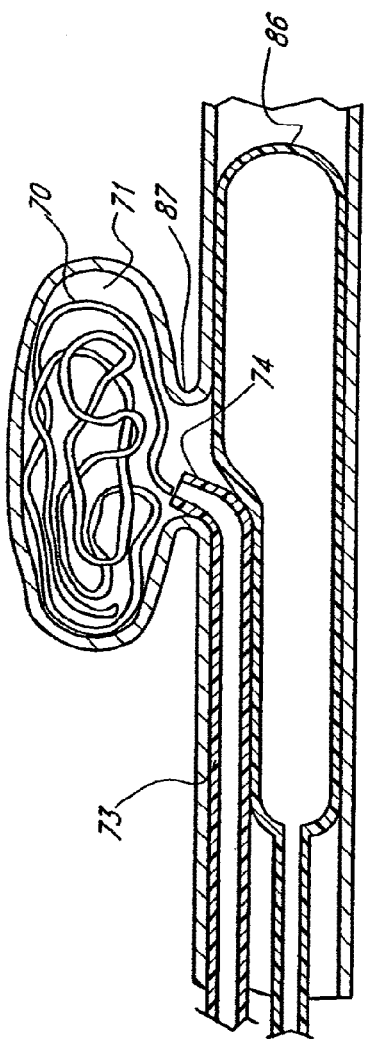

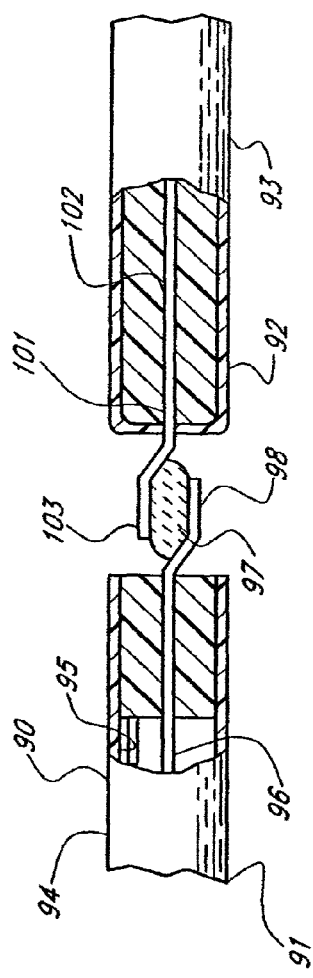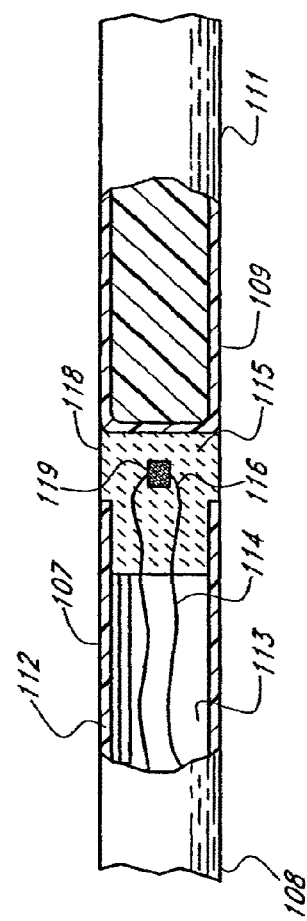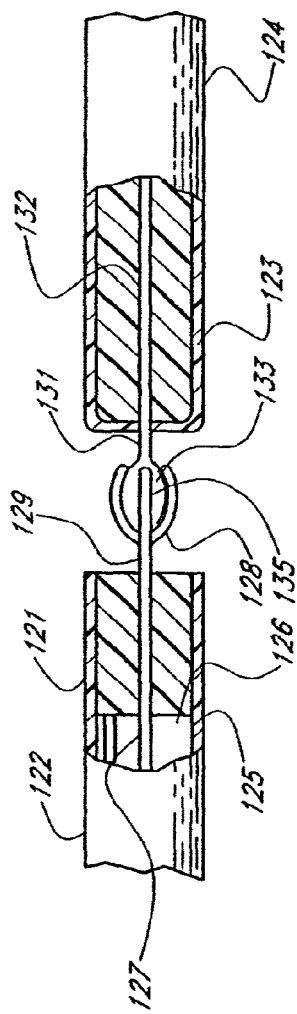

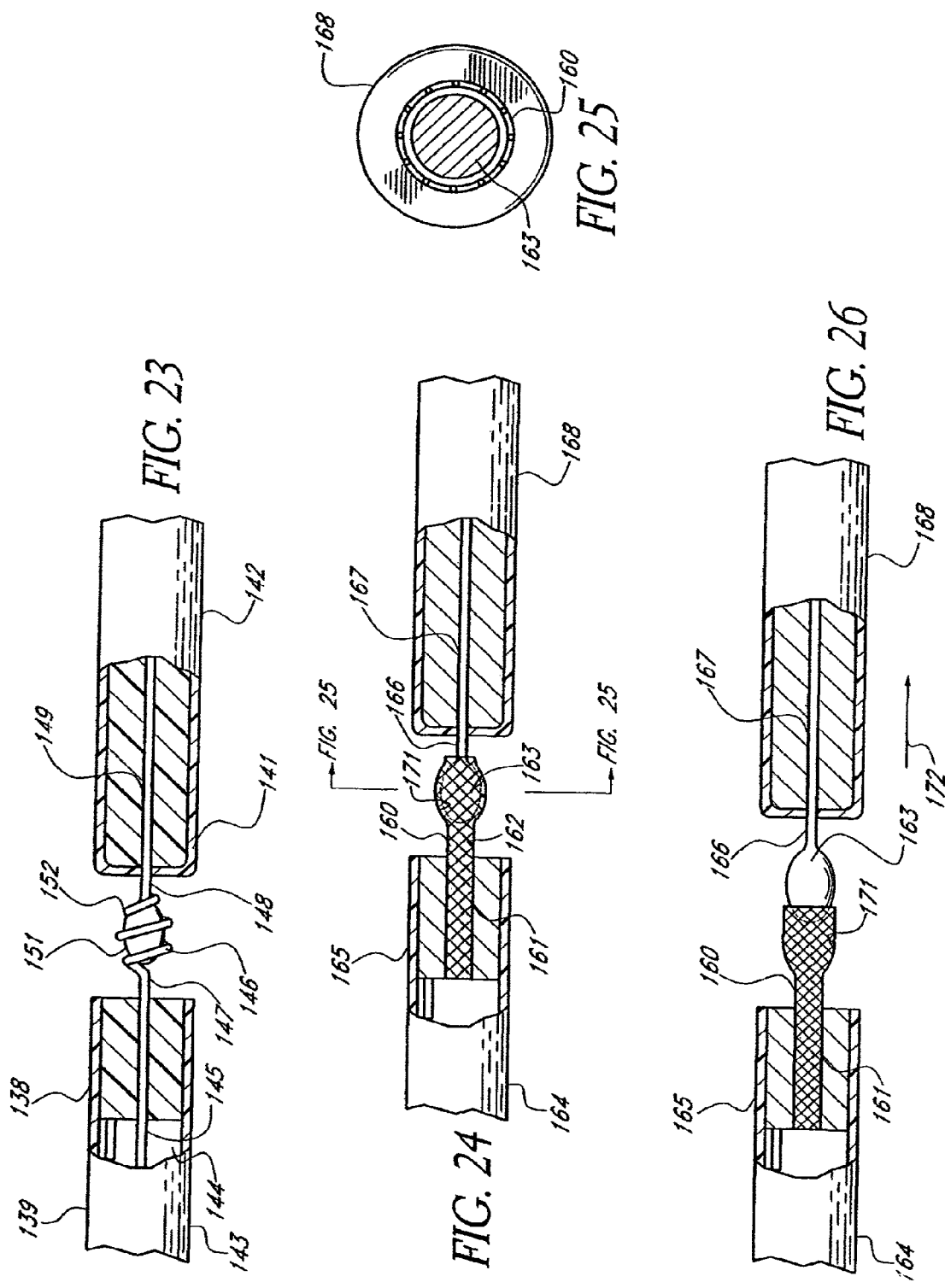

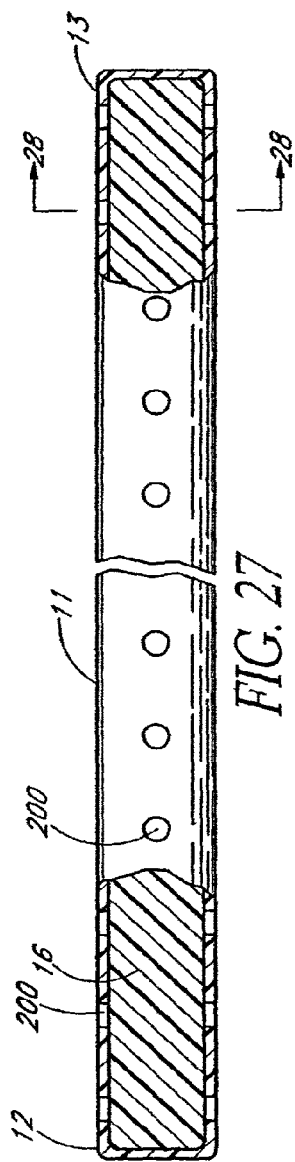
FIG. 27
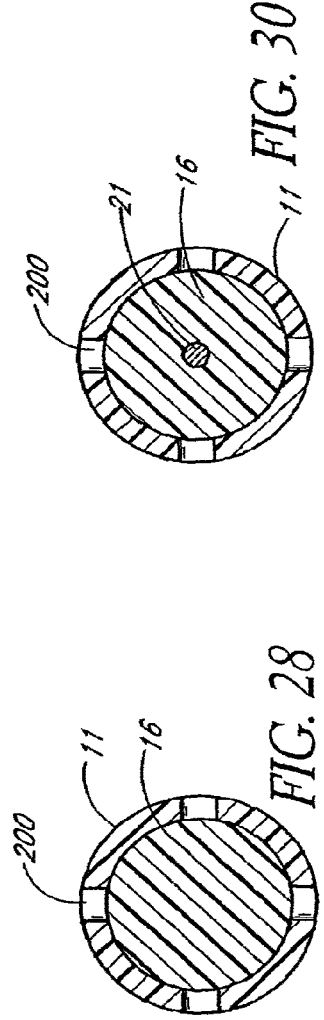
FIG. 28
FIG. 30
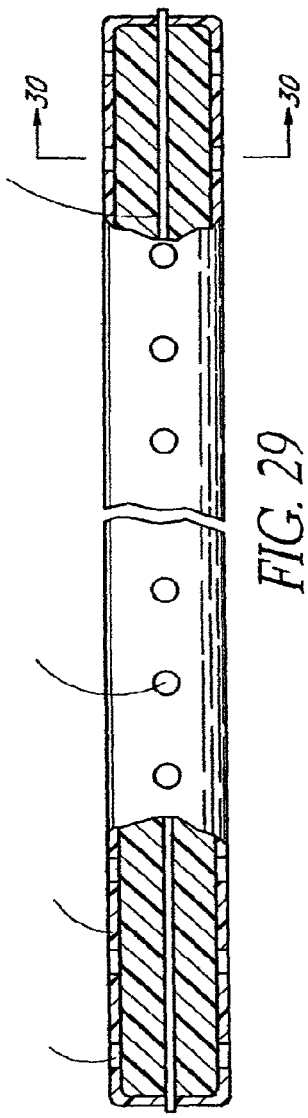
FIG. 29

INTRACORPOREAL OCCLUSIVE DEVICE AND METHOD

RELATED APPLICATIONS

The present application is a continuation of U.S. patent application Ser. No. 11/418,551 filed May 3, 2006 now U.S. Pat. No. 8,932,317 entitled Intracorporeal Occlusive Device And Method, which is a continuation of U.S. patent application Ser. No. 11/169,322 filed Jun. 28, 2005 entitled Intracorporeal Occlusive Device And Method (abandoned), which is a continuation of U.S. patent application Ser. No. 11/033,463 filed Jan. 11, 2005 entitled Intracorporeal Occlusive Device And Method (abandoned), which is a continuation of U.S. patent application Ser. No. 10/106,511 filed Mar. 25, 2002 entitled Intracorporeal Occlusive Device And Method (abandoned), which is a divisional of U.S. patent application Ser. No. 09/324,987 filed Jun. 2, 1999 entitled Intracorporeal Occlusive Device And Method (abandoned), all of which are incorporated herein by reference.

BACKGROUND

The present invention is generally directed to occlusion devices and, more specifically, to intracorporeal occlusion devices which can be used to treat a patient's blood vessels, intracorporeal conduits or other portions of a patient's body. A preferred embodiment can be used to treat intracranial aneurysms, arteriovenous fistulas, and other abnormalities within the cerebral vasculature.

Cerebral aneurysms and other cerebral vascular abnormalities present a significant medical problem to the population of the United States. It is estimated that the number of ruptured intracranial aneurysms yearly is in the tens of thousands, often with devastating consequences for the patient. For a patient who has been diagnosed with a cerebral aneurysm, there are a few treatment modalities currently available. An invasive surgical treatment can be used where access to the external portion of the aneurysm is achieved by placing the patient under general anesthesia, performing a craniotomy, and brain tissue retraction. Once access has been gained to the external surface of the aneurysm, the neck of the aneurysm can be clipped. Clipping the aneurysm neck prevents the ingress of blood into the aneurysm cavity which can lead to rupture. Because of the invasive nature of the procedure and the vulnerability of the brain tissue surrounding the aneurysm, this procedure carries a high degree of risk with concomitant mortality and morbidity rates. This risk is particularly high when the aneurysm has ruptured prior to the surgical intervention.

An alternative to the surgical method currently in use involves percutaneous endovascular intervention. This method generally involves accessing the cerebral aneurysm by means of an intravascular microcatheter which is advanced under fluoroscopic imaging over a guidewire or the like within the patient's arteries from a puncture site in the patient's leg or arm. The distal end of the microcatheter is guided over a guidewire within a patient's vasculature and disposed adjacent the neck of the aneurysm. The distal tip of the microcatheter can then be directed into the cavity of the aneurysm and appropriate occlusive devices then delivered from a port in the distal end of the microcatheter. Presently, the most common occlusive device delivered via microcatheter is a vaso-occlusive coil which consists of stainless steel or radiopaque metals such as gold or platinum, tantalum. The vaso-occlusive coils are typically manufactured in a manner similar to the distal coils of a coronary guidewire, having a coil wire material with a small diameter and a coil outer diameter suitable for delivery through a microcatheter. Such vaso-occlusive coils are often given a secondary shape or configuration whereby the coils can be straightened and delivered through the inner lumen of a microcatheter, but form a convoluted or random space filling structure once delivered from the distal end of the microcatheter. The endovascular delivery of vaso-occlusive coils through a microcatheter represents a significant advance in treating cranial aneurysms. However, the coils are hollow bodies, often made of relatively soft metals which are subject to compaction due to the pressure exerted on the deployed coils by the patient's blood flow. Compaction and reforming of the coils leaves them susceptible to dislodging and being displaced within the patient's vasculature, with the potential for causing distal embolization. In addition, compaction of the coils into the dome of the aneurysm or blood clot surrounding the coils can lead to reappearance and regrowth of the aneurysm. Finally, aneurysms with wide necks having a dome to neck dimension ratio of less than 2 to 1 often do not provide a morphology conducive to retention of coils within the aneurysm. Thus currently available coils are generally contraindicated for use in wide neck aneurysms. What has been needed is an intracorporeal space filling device which can be delivered by non-invasive methods, is not subject to compaction or reforming and which is suitable for implantation in wide neck aneurysms.

SUMMARY

The invention is directed generally to an intracorporeal space filling device and a delivery system for positioning and deploying the space filling device within a patient. The invention is also directed to a method for using the space filling device.

One preferred embodiment of the invention is an intracorporeal space filling device which has an elongate tubular shell with a lumen disposed within the shell. The lumen is in fluid communication with a first port in a first end of the shell, and a second port in a second end of the shell. A transmutable material is disposed within the lumen of the shell substantially filling the lumen. The transmutable material has properties which enable transformation from a non-rigid state to a substantially rigid state within a patient's body. The transmutable character of the transmutable material allows for a space filling device that is soft and flexible at the time of deployment into an intracorporeal cavity and rigid and substantially incompressible after being converted to a rigid state. Such a device can conform readily to the varied morphology of intracorporeal cavities and transmute to a substantially rigid mass upon activation or hardening of the transmutable material so as to be resistant to compression and reforming due to vascular or other types of pressures within a patient's body.

The elongate shell is generally made of a polymeric wall material and is sealed at either or both of the first and second ends. The transmutable material which fills the lumen of the shell can be selected from a variety of suitable polymers which can be made rigid or hardened by the application of a variety of energy types, such as light emitted from a laser or other source, radiofrequency energy, ultrasonic energy or other suitable means such as controlled changes in the pH of the material surrounding the transmutable material. The space filling device is typically configured for percutaneous delivery through a suitable microcatheter from an incision in a peripheral artery in a patient's arm or leg to a desired intracorporeal cavity, such as a cerebral aneurysm.

Optionally, the space filling device may have an elongated longitudinal member secured to and preferably coextensive with the elongate tubular shell of the device. Typically, the elongated longitudinal member is a thin wire member that may or may not be configured to give a secondary shape to the space filling device when in an unconstrained relaxed state. The secondary shape of the longitudinal member can be a convoluted, folded, coiled or twisted configuration or any other suitable space filling configuration when in an unconstrained state which is imparted to the intracorporeal space filling device to which the elongated longitudinal member is secured. When the device is in a linear constrained state or configuration, it may be advanced through an inner lumen of a microcatheter or other similar device for delivery to a desired site within a patient's body. Once the space filling device is removed from the constraint of the microcatheter, it again assumes the space filling secondary shape. The elongated longitudinal member can be made from a variety of suitable materials, including stainless steel and shape memory alloys such as nickel titanium (NiTi). The elongated longitudinal member can be disposed along a longitudinal axis of the space filling device, embedded in the transmutable material, encapsulated within the wall material of the elongate tubular shell, or adjacent an outside surface of the elongate tubular shell or any other suitable location on the device. Preferably the elongate longitudinal member is substantially parallel to the longitudinal axis of the elongate shell or intracorporeal space filling device. The elongated longitudinal member can also be configured to be heated by the passage of various types of energy therethrough. For example, an elongated longitudinal member made of NiTi alloy can be configured to be heated by the passage of electrical current, including radiofrequency, or ultrasonic energy through it. Heating of the elongated longitudinal member can be used to transmute or rigidify the transmutable material within the elongate shell and to act as a mechanism for detachment of the intracorporeal space filling device from the distal end of the delivery system.

In a preferred embodiment, the elongate tubular shell is configured to have an outer surface which is self adhering to create attachment points from contact point upon activation of the self adhering outer surface. Contact points along the length of the space filling device inevitably occur when the device is deployed within an intracorporeal cavity or channel and the space filling device assumes a folded or convoluted space filling configuration. The folded or convoluted space filling configuration may be due to the confinement of the void or channel, a secondary shape assumed by the device in a relaxed state, or both. The creation of attachment points results in a more rigid and stable space filling mass that is resistant to compaction and reforming.

The intracorporeal space filling device may optionally have a helical coil disposed about an outer surface of the elongate tubular shell. The helical coil may have properties similar to those discussed above with regard to the elongated longitudinal member. For example, the helical coil can be configured to impose a convoluted, folded or space filling secondary shape on the space filling device when in a relaxed unconstrained state. The helical coil may also be configured to heat or otherwise activate transmutation of the transmutable material when various forms of energy are passed through it such as electrical current, ultrasonic energy or the like. The materials of the helical coil may also be similar to those discussed above with regard to the elongated longitudinal member.

In an alternative embodiment, the space filling device has a transmutable material disposed about an elongated longitudinal member without an outer shell so that the transmutable material is exposed when the device is deployed within a patient's body. The elongated longitudinal member can have properties similar to those of the elongated longitudinal members discussed above. For example, the elongated longitudinal member can be made of a thin wire with a secondary shape. The secondary shape can be imparted on the space filling device when the device is in an unconstrained state. Secondary shapes can include convoluted or folded space filling configurations. Exposure of an outside surface of the transmutable material allows the transmutable material to adhere to itself upon transmutation at attachment points where different portions of the space filling device make contact due to the secondary shape assumed. When the space filling device is deployed in an intracorporeal cavity and assumes a folded, bunched or convoluted configuration due to a secondary shape of the elongated longitudinal member or the natural confinement of the cavity, inevitably, certain portions of the space filling device will make physical contact with other portions of the device. As such, the transmutable material of these portions will make contact at contact points and will cross-link, bond, or self adhere to each other to form attachment points upon transmutation of the transmutable material. The cross-linking or bonding of the device at attachment points results in a rigid mass which is resistive to compression and reforming. The self adhering property of the outside surface of the transmutable material can be as a result of the intrinsic properties of the transmutable material, or as a result of a coating applied to the transmutable material with self adhering properties.

In another embodiment, the intracorporeal space filling device has a plurality of beads connected to at least one adjacent bead by a flexible member with connections to adjacent beads being configured to produce a linear array of the beads. Each bead has a transverse dimension and is generally spaced within one transverse dimension of adjacent beads, however, other appropriate spacings are possible. The space filling device of interconnected beads is generally configured for percutaneous delivery through a microcatheter or the like from an incision in a peripheral artery of a patient to a desired cavity within the patient's vasculature such as a cerebral aneurysm. The individual beads typically have a generally spherical shape, but can also be substantially elliptical or elongated. The beads can be made from any suitable material, but are preferably made from a polymer material, and more preferably a transmutable polymer material. In a particular embodiment, the beads may have an outer shell which defines a cavity which optionally contains suitable filler material. Suitable filler materials include biocompatible fluids such as a saline, silicone and the like, and polymers such as a transmutable material similar to the transmutable material discussed above.

Embodiments with beads of exposed transmutable material can be cross-linked or bonded to adjacent beads which are in contact at the time of transmutation at a desired site within a patient's body. Adjacent beads in contact while deployed within a desired location within a patient can adhere or bond together and create attachment points upon transmutation of the transmutable material. The attachment points create a more stable and rigid mass than would be achieved by transmutation of the beads without attachment points.

The flexible member connecting adjacent beads may consist of interconnected portions of a polymer wall material of the outer shell of each adjacent bead. The flexible member may also be an elongated longitudinal member disposed substantially along a longitudinal axis of the space filling device and being substantially coextensive with at least two adjacent beads of the space filling device. In embodiments of the space filling device having a flexible member consisting of an elongated longitudinal member, the elongated longitudinal member may be a thin wire, preferably of a shape memory alloy. The thin wire longitudinal member can be configured to be heated by a passage of energy through it in order to activate transmutation of transmutable material disposed thereon. The elongated longitudinal member may also be configured to have a secondary shape or space filling configuration in a relaxed state as discussed above with regard to other elongated longitudinal members. The secondary shape or space filling configuration of the elongated longitudinal member would be imparted to the space filling device as a whole when in an unconstrained relaxed state.

The intracorporeal space filling devices discussed above are generally deployed at a desired site within a patients body by disposing the distal end of a microcatheter or the like such that a distal port in the distal end of the microcatheter is directed to a desired cavity or channel within a patient. The space filling device is then distally advanced within the inner lumen of the microcatheter, preferably by means of a delivery system which has an elongate shaft with a detachment mechanism disposed on the distal end of the system. The detachment mechanism is detachably secured to a first end of the space filling device which provides a detachable connection and allows for remote advancement and retraction of the space filling device within the patient prior to detachment. The space filling device is then distally advanced out of a port in the distal end of the microcatheter and into the cavity or channel of the patient. When the space filling device is appropriately positioned, the transmutable material within the device is activated so as to be hardened or rigidified, and the device detached from the delivery system. Preferably, the space filling device is detached by a detachment mechanism utilizing degradation of a polymer link between the delivery system and the first end of the space filling device. Degradation of the polymer link may be accomplished by a chain cleavage reaction which can be initiated by heating of the polymer link. Alternative detachment mechanisms include mechanical detachment, electrolytic detachment, detachment by shape memory alloy or shape memory polymer activation via application of RF energy, laser energy or ultrasonic energy, heating of a hot melt adhesive joint, ultrasonic link degradation, hydrokinetic pressure activation of a mechanical retention device, and the like.

During deployment of a space filling device, a blocking balloon may be deployed adjacent the opening of an intracorporeal void and distal end of a microcatheter disposed within the void prior to distally advancing the space filling device from the distal end of the microcatheter into the cavity. The blocking balloon prevents egress of the space filling device from within the cavity during deployment of the device.

These and other advantages of the invention will become more apparent from the following detailed description of the invention when taken in conjunction with the accompanying exemplary drawings.

BRIEF DESCRIPTION

FIG. 5 is a longitudinal sectional view of an intracorporeal space filling device having features of the invention.

FIG. 6 is a transverse cross sectional view of the intracorporeal space filling device of FIG. 5 taken at lines 6-6 of FIG. 5.

FIG. 7 is a longitudinal sectional view in of an intracorporeal space filling device similar to the device of FIG. 1, but including an outer coil member.

FIG. 8 is a transverse cross sectional view of the device of FIG. 7 taken along lines 8-8 in FIG. 7.

FIG. 12 is a longitudinal sectional view of an intracorporeal space filling device having features of the invention.

FIG. 13 is a transverse cross sectional view of the intracorporeal space filling device of FIG. 12 taken at lines 13-13 of FIG. 12.

FIG. 14 is a longitudinal sectional view of an intracorporeal space filling device having features of the invention.

FIG. 15 is a transverse cross sectional view of the intracorporeal space filling device of FIG. 14 taken at lines 15-15 of FIG. 14.

FIG. 16 is a schematic view in partial longitudinal section of a microcatheter over a guidewire disposed within a patient's blood vessel.

FIG. 17 is a schematic view in partial section of the distal end of a microcatheter disposed within the neck of an aneurysm.

FIG. 18 is a schematic view in partial section of the distal end of a microcatheter disposed within an aneurysmal cavity with an intracorporeal space filling device deployed within the aneurysm.

FIG. 19 is a schematic view in partial section of a blocking balloon deployed adjacent an aneurysm with the distal end of a microcatheter disposed within the aneurysm and an intracorporeal space filling device disposed within the aneurysm.

FIG. 20 is an elevational view in partial section of a first end of an intracorporeal space filling device detachably secured to a distal end of a delivery system having features of the invention.

FIG. 21 is an elevational view in partial section of a first end of an intracorporeal space filling device detachably secured to a distal end of a delivery system having features of the invention.

FIG. 22 is an elevational view in partial section of a first end of an intracorporeal space filling device detachably secured to a distal end of a delivery system having features of the Invention.

FIG. 23 is an elevational view in partial section of a first end of an intracorporeal space filling device detachably secured to a distal end of a delivery system having features of the invention.

FIGS. 24-26 depict an alternative embodiment of a capture element for detachment of the space filling device.

FIG. 27 is a longitudinal sectional view of an alternate embodiment of the device of FIG. 1 further including apertures.

FIG. 28 is a cross sectional view of the device of FIG. 27.

FIG. 29 is a longitudinal sectional view of an another embodiment similar to the device of FIG. 3 further including apertures.

FIG. 30 is a cross sectional view of the device of FIG. 29 taken along line 30-30.

DETAILED DESCRIPTION

Figure 1:
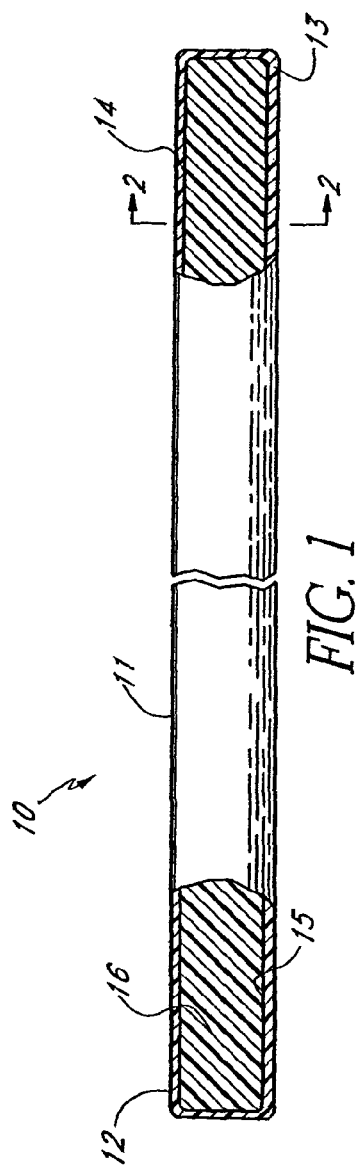
FIG. 1 is a longitudinal sectional view of an intracorporeal space filling device having features of the invention.

FIG. 1 illustrates an intracorporeal space filling device 10 having features of the invention. The intracorporeal space filling device 10 has an optional elongate tubular shell 11 with a first end 12 and a second' end 13, the elongate shell being formed of a wall material 14. There is a lumen 15 disposed within the elongate tubular shell 11 which has transmutable material 16 disposed therein.

The elongate tubular shell 11 can be made from a variety of materials including metals and polymers. Suitable metals for the elongate tubular shell include stainless steel, NiTi, gold, platinum, tantalum, palladium, alloys thereof and the like. If a metal or other rigid material is used, methods such as forming slots or grooves in the wall material of such an elongate tubular shell may be used to achieve a desired longitudinal flexibility of the elongate tubular shell 11. Suitable polymers for the elongate tubular shell 11 can include polyurethane, polyethylene, nylon, polyimide, polyamide, polytetrafluoroethylene, polyester, polypropylene and the like. The elongate tubular shell 11 may be sealed and impermeable to the transmutable material 16, so as to prevent the egress of the transmutable material from within the shell to the surrounding environment.

In one preferred embodiment features of which are depicted in FIGS. 27 and 28, the elongate tubular shell 11 has at least one aperture 200 which exposes the transmutable material 16 and allows the transmutable material to make contact with adjacent portions of the space filling device or other space filling devices so as to permit self adhering or bonding upon transmutation of the transmutable material. The apertures in the elongate tubular shell 11 can be in the form of transverse or longitudinal slots or grooves, circular or otherwise configured holes, or the like. The apertures may be relatively far apart relative to the size of the apertures, or they may be relatively close together and numerous so as to form a mesh pattern or other suitable pattern of fenestration which facilitates exposure of the transmutable material 16 but maintains the overall elongated structure of the space filling device 10. Similar apertures may be appropriate for any of the various embodiments of space filling devices discussed herein having outer shell structures.

The dimensions of the space filling device 10 and elongate tubular shell 11 are generally appropriate for percutaneous delivery via a microcatheter to a desired site within a patient's vasculature, however, other suitable dimensions and configurations are contemplated. The length of the space filling device 10, and all other embodiments of space filling devices discussed herein generally, can be from about 0.5 to about 50 cm, preferably about 2 to about 30 cm. It should be noted that the morphology of the sites being filled or otherwise treated by the present invention vary greatly. Embodiments of the invention for use treating cerebral aneurysms may be made available in a variety of sizes and lengths so that most of the anticipated morphologies can be accommodated. For example, a space filling device 10, and other space filling devices discussed herein generally, configured for treatment of cerebral aneurysms, or the like, may be made available in lengths of 2, 5, 10, 15, 20, 25, 30, 35 and 40 cm. In this way, a wide range of aneurysm volumes can be appropriately treated.

A transverse dimension of the space filling device 10, and of all other embodiments of space filling device discussed herein generally, can be from about 0.005 to about 0.25 inches, preferably about 0.01 to about 0.038 inches, and more preferably about 0.014 to about 0.018 inches. In other preferred embodiments of the invention, the transverse dimension of the space filling device can be from about 0.004 to about 0.02 inches, preferably about 0.008 to about 0.012 inches. The thickness of the wall material 14 of the elongate tubular shell 11 can be from about 0.0001 to about 0.01 inches, preferably about 0.0005 to about 0.002 inches, and more preferably about 0.001 to about 0.0015 inches.

The transmutable material 16 disposed within the elongate tubular shell 11 is preferably a material that can be transmuted by polymerization, crystallization or other suitable process from a non-rigid liquid, gel or granular state to a rigid state. Some of the materials suitable for this application are discussed generally in U.S. Pat. No. 5,334,201, K. Cowan, and U.S. Pat. No. 5,443,495, P. Buscemi, et al., which are hereby incorporated by reference in their entirety. Transmutation of the transmutable material can be achieved or activated by the application of a suitable type of energy to the transmutable material. Suitable types of energy include electromagnetic energy in the form of light, DC current, AC current, RF current or the like in addition to ultrasonic energy. Energy may also be applied directly or indirectly in the form of heat to cause transmutation. Transmutation may also be activated by altering the chemistry of the environment surrounding the transmutable material such as by changing the pH or by injection of a catalyst into the transmutable materials, either directly or indirectly by injection or introduction into the surrounding tissue or bodily fluid such a blood. With regard to the embodiment of FIG. 1, laser or RF energy is preferably applied to the outer surface of the elongate tubular shell and transmutable material to cause transmutation. The outer dimensions of the transmutable material 16 are generally similar to the cavity dimensions of the elongate tubular shell 11. As an alternative to the transmutable material 16, any suitable biocompatible filler material may be used such as saline, silicone or the like. Such alternative filler materials may be used within any of the suitable embodiments of space filling devices described herein, either as an alternative to a transmutable material, or in addition to a transmutable material. Embodiments of the invention suitable for alternative filler materials are generally those embodiments having a shell structure configured to confine the alternative filler materials.

In embodiments of the space filling device 10 where the transmutable material 16 is exposed, that is, where the optional elongate tubular shell 11 is not present, or portions of the elongate tubular shell 11 are not present at aperture sites, it is preferable that the transmutable material 16 be self adhering in a fluid field, such as blood or saline. In this way, when the device 10 is deployed within an intracorporeal cavity or channel and folds back on itself as a result of the confinement of the cavity or channel, any contact points between transmutable material where the device is folded on itself and making mechanical contact will become attachment points upon transmutation of the transmutable material by bonding or adhering to itself at the contact points. The attachment points result in a more stable space filling mass that is resistant to compaction and reforming.

Suitable substances generally for the transmutable material 16 include methacrylate compounds, linear polyester, silicone, cyanoacrylates, polyisocyanate, u.v. curable acrylates, moisture cure silicones, dimethyl sulfoxide, thioisocyanate aldehyde, isocyanate, divinyl compounds, epoxide acrylates, succinimidyl azido salicylate, succinimidyl azidobenzoate, succinimidyl dithio acetate, azidoiodobenzene, flouronitrophenylazide, salicylate azides, benzophenonemaleimide, and the like.

Figure 2:
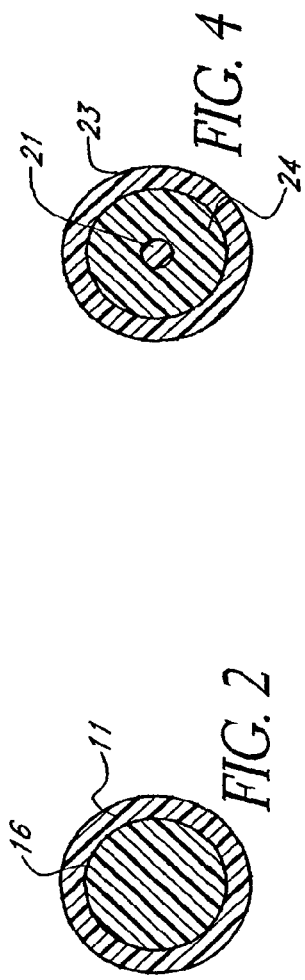
FIG. 2 is a transverse cross sectional view of the intracorporeal space filling device of FIG. 1 taken at lines 2-2 of FIG. 1.

FIG. 2 is a transverse cross sectional view of the intracorporeal space filling device 10 of FIG. 1. The transmutable material 16 is disposed within the optional elongate tubular shell 11 of the device. The cross section of FIG. 2 is shown as substantially round, however, other suitable cross sectional configurations can be used such as elliptical, triangular or square.

Figure 3:
FIG. 3 is a longitudinal sectional view of an intracorporeal space filling device having features of the invention.
Figure 4:
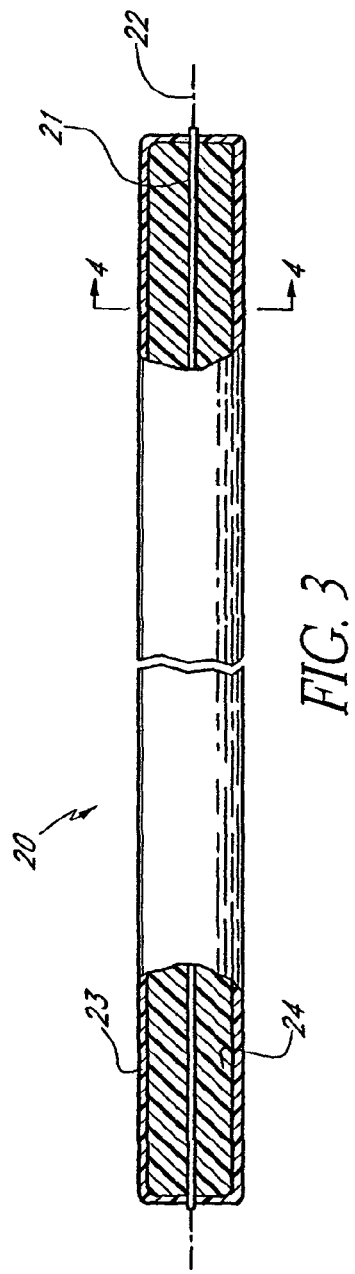
FIG. 4 is a transverse cross sectional view of the intracorporeal space filling device of FIG. 3 taken at lines 4-4 of FIG. 3.

FIGS. 3 and 4 illustrate an intracorporeal space filling device 20 similar to the embodiment of FIG. 1, with the addition of an elongated longitudinal member 21 disposed along a longitudinal axis 22 of the optional elongate tubular shell 23. The materials, dimensions, and features of the elongated tubular shell 23 of FIGS. 3 and 4 can be similar to those of the elongated tubular shell 11 of FIGS. 1 and 2. The materials and dimensions of the transmutable material 24 can be similar to those of the transmutable material 16 discussed above. Typically, the elongated longitudinal member 21 is a thin wire member that is configured to give a secondary shape to the space filling device when in an unconstrained relaxed state. The longitudinal member 21 can have a secondary shape of a convoluted, folded, coiled or twisted configuration or any other suitable space filling configuration when in an unconstrained state. This configuration is imparted to the intracorporeal space filling device 20 to which the elongated longitudinal member 21 is secured. When the device 20 is in a linear constrained state or configuration, it may be advanced through an inner lumen of a microcatheter or other similar device for delivery to a desired site within a patient's body. Once the space filling device 20 is removed from the constraint of the microcatheter, it again assumes the space filling configuration. The space filling device 20, and all other space filling devices described herein generally which are configured to have a secondary space filling shape, may have a variety of nominal transverse dimensions or diameters when in a secondary shape. In order to conform to a wide variety of intracorporeal morphologies, the space filling device may have a secondary shape with a transverse dimension of between about 1 to about 20 mm. A typical space filling device maybe made with a secondary shape having a transverse dimension of between 1 and 20 mm, in 1 mm increments.

The elongated longitudinal member 21 can be made from a variety of suitable materials, including stainless steel and shape memory alloys such as nickel titanium (NiTi). The length of the elongated longitudinal member 21 can be from about 0.5 to about 50 cm, preferably about 1 to about 20 cm, and more preferably about 5 to about 15 cm. It is preferable that the elongated longitudinal member 21 be coextensive with the length of the elongated tubular shell 23 and with the space filling device generally. Thus, the elongated longitudinal member may have any of the lengths discussed herein with regard to space filling devices. The transverse dimension of the elongated longitudinal member 21 can be from about 0.0005 to about 0.01 inches, preferably about 0.001 to about 0.003 inches, and more preferably about 0.0015 to about 0.002 inches. The cross section of the elongated longitudinal member is generally round, however, other configurations are contemplated. Alternative cross sectional shapes for the elongated longitudinal member include elliptical, rectangular, as would be found if a flat ribbon wire used, triangular, square and the like. The various cross sections can be chosen to give a desired preferred bend axis or axes along the length of the member. Preferably the elongate longitudinal member is substantially parallel to the longitudinal axis 22 of the elongate shell or intracorporeal space filling device. The elongated longitudinal member 21 can also be configured to be heated by the passage of various types of energy therethrough. For example, an elongated longitudinal member 21 made of NiTi alloy can be configured to be heated by the passage of electrical current through it. Heating of the elongated longitudinal member 21 can be used to transmute or rigidify the transmutable material within the elongate tubular shell 23 and to act as a mechanism for detachment of the intracorporeal space filling device 20 from a distal end of a delivery system. In an alternate embodiment, the shell 23 includes apertures 200 for exposing the transmutable material, as described in reference to FIGS. 27 and 28.

FIGS. 5 and 6 show an embodiment of an intracorporeal space filling device 30 similar to the embodiment of FIGS. 3 and 4 but having an elongated longitudinal member 31 encapsulated within a wall material 32 of the elongated tubular shell 33. The materials, dimensions and features of the elongated tubular shell 33 and elongated longitudinal member 31 of FIGS. 5 and 6 are similar to those of the elongated tubular shell 23 and elongated longitudinal member 21 of FIGS. 3 and 4. The elongated longitudinal member 31 may also be secured to an outside surface 34 or inside surface 36 of the elongate tubular shell 33 by an adhesive or other suitable means. A transmutable material 35 disposed within the elongate tubular shell 33 can have properties and dimensions similar to or the same as those of transmutable materials 16 and 24 of FIGS. 1-4 above.

FIGS. 7 and 8 illustrate an intracorporeal space filling device 40 similar to that of FIGS. 1 and 2, but with a helical coil 41 disposed about an outside surface 42 of the elongated tubular shell 43. The helical coil 41 of FIGS. 7 and 8 may have some properties similar to those discussed above with regard to the elongated longitudinal members 21 and 31 of FIGS. 3-6. The helical coil 41 can be configured to impose a convoluted, folded or space filling configuration on the space filling device 40 when in a relaxed unconstrained state. The helical coil 41 may also be configured to heat when various forms of energy are passed through it. The materials of the helical coil 41 can be any suitable metal, composite or polymer including shape memory alloys such as NiTi or high strength alloys such as stainless steel. The type and dimensions of the material from which the helical coil 41 is made can be similar to the elongated longitudinal member 31 discussed above. A transmutable material 44 is disposed within the elongated tubular shell 43 and can have properties similar or identical to the properties of transmutable materials 16, 24 and 35 of FIGS. 1-6 above.

Figure 9:
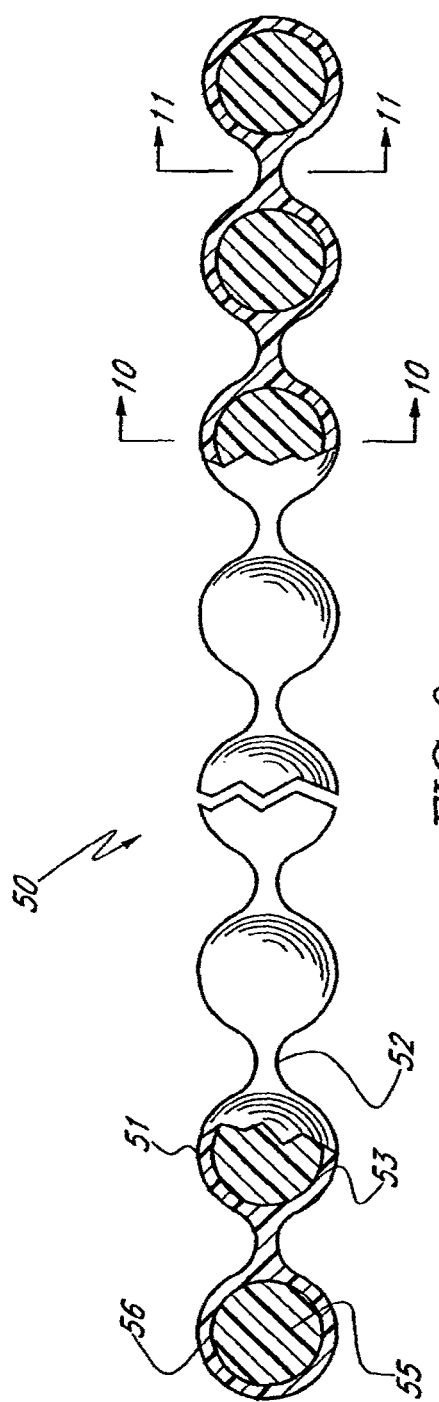
FIG. 9 is a longitudinal sectional view of an intracorporeal space filling device having features of the invention.
Figure 11:
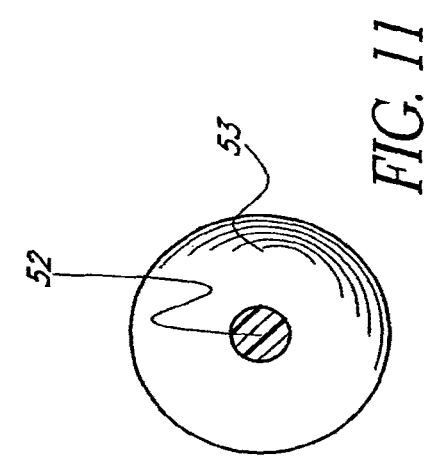
FIG. 11 is a transverse cross sectional view of the intracorporeal space filling device of FIG. 9 taken at lines 11-11 of FIG. 9.
Figure 10:
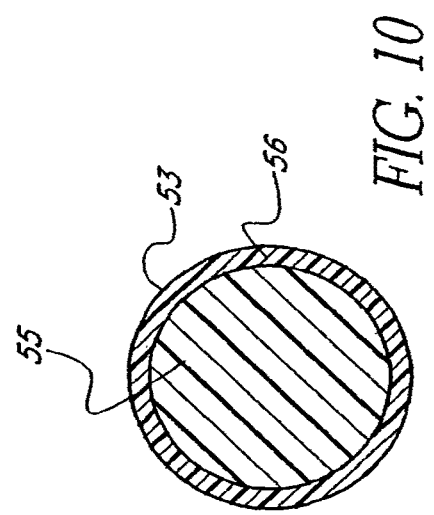
FIG. 10 is a transverse cross sectional view of the intracorporeal space filling device of FIG. 9 taken at lines 10-10 of FIG. 9.
Figure 31:
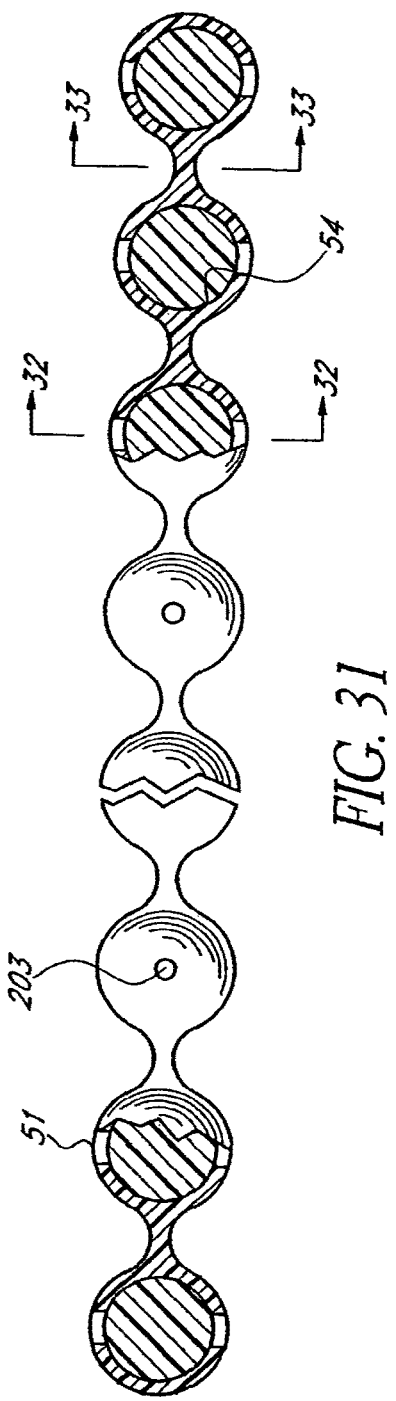
FIG. 31 is a longitudinal sectional view of an another embodiment similar to the device of FIG. 9 further including apertures.
Figure 33:
FIG. 33 is a cross sectional view of the device of FIG. 30 taken along line 33-33.
Figure 32:
FIG. 32 is a cross sectional view of the device of FIG. 30 taken along line 32-32.

FIGS. 9-11 depict an alternative embodiment of an intracorporeal space filling device 50 having a plurality of beads 51 secured to each other in a linear configuration. The intracorporeal space filling device 50 has a plurality of beads 51 connected to at least one adjacent bead by a flexible member 52 with connections to adjacent beads preferably being configured to produce a linear array of the beads. Each bead 51 has a transverse dimension and is generally spaced within one transverse dimension of adjacent beads, however, other appropriate spacings are possible. The space filling device 50 is generally configured for percutaneous delivery through a microcatheter or the like from an incision in a peripheral artery of a patient to a desired cavity within the patient's vasculature such as a cerebral aneurysm. The individual beads 51 typically have a generally spherical shape, but can also be substantially elliptical, with the elliptical shape optionally being elongated longitudinally to a length of multiple transverse dimensions. The beads 51 can be made from a rigid homogeneous polymer material, but are preferable made from an outer shell 53 which defines a cavity 54 such as is shown in FIGS. 9-11. The outer shell 53 can be made from a variety of materials including metals and polymers. Suitable metals for the shell 53 include stainless steel, NiTi, gold, platinum, tantalum, palladium, alloys thereof and the like. If a metal or other rigid material is used, methods such as forming slots or grooves in the wall material of the shell may be used to achieve a desired longitudinal flexibility. Suitable polymers for the shell 53 can include polypropylene and the like. The outer shell 53 as shown in FIGS. 31-33 may have apertures 203 similar to those of space filling device 10 described above for exposing portions of transmutable material contained therein which facilitates self adherence and the creation of attachment points upon transmutation of the transmutable material.

The cavity 54 optionally contains a transmutable material 55 similar to the transmutable materials 16, 24, 35 and 44 discussed above. The transmutable material 55 is preferably a material that can be transmuted by polymerization, crystallization or other suitable process from a non-rigid liquid, gel or granular state to a rigid state. Transmutation of the transmutable material 55 can be achieved or precipitated by the application of a suitable type of energy to the transmutable material such as electromagnetic energy in the form of light, DC current, AC current, RF or ultrasonic energy. Energy may also be applied directly or indirectly in the form of heat to cause transmutation. Other methods of causing or precipitating transmutation can include altering the pH of the surrounding environment of the transmutable material, or injecting a catalyst into the transmutable material directly, or indirectly by injecting a catalyst into the environment of the transmutable material.

The dimensions of the space filling device 50 overall are similar to those of the previously discussed embodiments. The thickness of the wall material 56 of the outer shell 53 can be from about 0.0001 to about 0.01 inches, preferably about 0.0005 to about 0.002 inches, and more preferably about 0.001 to about 0.0015 inches. The wall material 56 of the outer shell 53 of the beads 51 and the transmutable material 55 disposed within the outer shell can be similar to the materials of the elongate tubular shell 11 and transmutable material 16 of the embodiment of FIG. 1.

The flexible member 52 connecting adjacent beads may consist of interconnected portions of a polymer wall material 56 of the outer shell 53 of each adjacent bead as shown in FIGS. 9-11. As shown in FIGS. 12-13, an intracorporeal space filling device 60 may have flexible members 61 that consist of portions of an elongated longitudinal member 62 disposed substantially along a longitudinal axis 63 of the space filling device 60 and being substantially coextensive with at least two adjacent beads 64 of the space filling device. The beads 64 of the space filling device 60 are made of a polymer material 65 which is a transmutable material. The exposed outer surface of the transmutable material of the beads 64 is self adhering in a fluid field, such as blood or saline. When the space filling device 60 is deployed within a body cavity and folds back on itself as a result of the confinement or secondary shape, any contact points where the device is folded on itself making mechanical contact will become attachment points upon transmutation of the transmutable material of the beads 64. The attachment points result in a more stable space filling mass which is resistant to compaction and reforming.

The elongated longitudinal member 62 may be a thin wire, preferably of a shape memory alloy that can be configured to be heated by a passage of energy through it. The elongated longitudinal member 62 shown in FIGS. 12-13 can have similar dimensions and properties to the elongated longitudinal members 21 and 31 shown in FIGS. 3-6. These properties can include a secondary shape, shape memory properties, and heating upon a passage of energy through the elongate longitudinal member 62. In addition, the elongated longitudinal member 62 can have a variety of cross section configuration including round, square, rectangular and the like.

FIGS. 14 and 15 depict an intracorporeal space filling device 66 which has beads 67 attached in a substantially linear array by an elongate longitudinal member 68. The beads 67 have an outer shell 69 which is optionally filled with a transmutable material 69A. The dimensions and materials of beads 67 can be similar to those of beads 51 discussed above with regard to FIGS. 9-11. The materials and dimensions of longitudinal member 68 can be similar to those of elongated longitudinal member 62 discussed above with respect to FIGS. 12 and 13.

FIGS. 16-19 schematically depict a procedure whereby an intracorporeal space filling device 70 is deployed within an intravascular cerebral aneurysm 71 of a patient by percutaneous means through a lumen 72 of a microcatheter 73. The distal end 74 of microcatheter 73 is advanced over a guidewire 75 through a patient's vasculature and artery 76 to an aneurysm 71. The space filling device 70 is then distally advanced within an inner lumen 72 of the microcatheter 73, preferably by means of a delivery system 77. Delivery system 77 has an elongate shaft 80 with a detachment mechanism 81 disposed on the distal end 82 of the system. The detachment mechanism 81 is detachably secured to a first end 83 of the space filling device 70 which allows proximal manipulation of the delivery system 77 to control axial advancement and retraction of the space filling device within the microcatheter 73 and the patient. The space filling device 70 is then distally advanced out of a port 84 in the distal end 74 of the microcatheter 73 and into the aneurysm 71.

When the space filling device 70 is appropriately positioned, transmutable material of device 70 is transmuted to a rigid state, and the space filling device 70 detached from the delivery system 77. Transmutation of the transmutable material may take place prior to, during or after detachment of the space filling device from the detachment mechanism. The space filling device 70 is detached by degradation of a polymer link 85 between the delivery system 77 and the first end 83 of the space filling device, preferably by a chain cleavage reaction which can be initiated by heating of the polymer link 85. Although the illustrated method of detachment of the space filling device 70 is chain cleavage degradation of a polymer link 85, any suitable detachment, electrolytic detachment, shape memory metal or polymer activation via a temperature change by application of RF energy, laser energy, ultrasonic energy, heating of a hot meld adhesive joint, ultrasonic joint degradation, hydrokinetic activation of a mechanical retaining device, and the like. Various detachment mechanisms known in the art are discussed in U.S. Pat. No. 5,722,989, J. Fitch et al., U.S. Pat. No. 5,018,407, G. Geremia et al., U.S. Pat. No. 5,217,484, M. Marks, and U.S. Pat. No. 5,423,829, P. Pham, which are hereby incorporated by reference.

Upon proper positioning of the space filling device 70 within the aneurysm 71, the device will assume a space filling folded or convoluted configuration due to the confinement of the aneurysm cavity, a secondary shape imparted to the device by an elongated longitudinal member having a secondary shape, or both of these. As a result of the folded or convoluted configuration of the space filling device, contact points 78 as shown in the enlarged view of FIG. 18A will result. Upon transmutations of the transmutable material of the device 70, contact points 78 cross-link, bond, self adhere or the like to become attachment points which result in a more stable and rigid transmuted space filling device than would result without such attachment points. Such a configuration resists compaction and repositioning after deployment, and facilitates use in aneurysms or other bodily cavities having a dome to neck ratio of less than 2 to 1. It is believed that upon proper deployment of the space filling device of the present invention, flow of blood throughout the aneurysm will be sufficiently reduced for a sufficient time to allow clot formation within the aneurysm cavity. Eventually, the clot will organize and endothelial growth over the clot in the neck area of the filled aneurysm will ensue, completing the healing process. The resistance to compaction and reforming by the space filling device of the present invention is believed to facilitate the reduction of blood flow throughout the aneurysm for a sufficient time for this healing process to occur.

As shown in FIG. 19, a blocking balloon 86 may be deployed adjacent the neck 87 of aneurysm and distal end 74 of the microcatheter 73 prior to distally advancing the space filling device from the distal end of the microcatheter into the aneurysm. The blocking balloon 86 facilitates maintaining the space filling device 70 within the aneurysm 71 prior to transmutation of the transmutable material within the space filling device. In this way, aneurysms having a greater neck to dome ratio can be effectively treated.

FIG. 20 shows a distal end 90 of a delivery system 91 detachably secured to a first end 92 of a space filling device 93 having features of the invention. The distal end 90 of the delivery system has an elongate tubular shaft 94 with an inner lumen 95 disposed therein. A detachment signal conduit 96 is disposed within the inner lumen 95 of the shaft and is connected to a degradable polymer link 97 at a distal extremity 98 of the conduit. A first end 101 of an elongate longitudinal member 102 is detachably secured to the degradable polymer link 97 to form a detachment mechanism 103. The detachment mechanism 103 can be activated by means of a signal transmitted through the detachment signal conduit 96 which degrades the polymer link and releases the space filling device 93 from the delivery system 91. The polymer link 97 is preferably degraded by a chain cleavage or scission reaction. Materials and Methods suitable for such a mechanism are discussed generally in U.S. Pat. No. 5,443,495 which has been incorporated herein. The detachment signal transmitted through the detachment signal conduit 96 is preferably a radiofrequency signal that initiates a chain cleavage reaction in the degradable polymer link 97, however, other signals or energy delivery may be used such as alternating or direct electric current, ultrasonic energy, laser energy or any other form of electromagnetic radiation or the like. The detachment signal conduit 96 may be a single, double or multiple pole wire, coaxial cable, fiber optic, elongate ultrasonic energy transmitter, such as a solid rod of metal, glass or composite or the like. If a single pole wire is used, a current flow path may be established by the application of a conductive pad to a suitable portion of the patient's body, preferably with a highly conductive gel between the conductive pad and the patient's skin. Alternatively, a conductive needle, such as a stainless steel 18 gauge needle, may be inserted into a suitable site of the patient to act as a ground. These grounding techniques may be used for any port of the invention requiring an electric current flow path, including the heating of elongated longitudinal or helical members for transmutation of transmutable materials.

FIG. 21 shows a distal end 107 of a delivery system 108 detachably secured to a first end 109 of a space filling device 111 having features of the invention. The distal end 107 of the delivery system 108 has an elongate tubular shaft 112 with an inner lumen 113 disposed therein. A detachment signal conduit 114 is disposed within the inner lumen 113 of the shaft 112 and is connected to a degradable polymer link 115 at a distal extremity 116 of the conduit. The first end 109 of the space filling device 111 is detachably secured to the degradable polymer link 115 to form a detachment mechanism 118. The detachment mechanism 118 can be activated by means of a signal transmitted through the detachment signal conduit 114 which degrades the polymer link 115 and releases the space filling device 111 from the delivery system 108. The detachment signal transmitted through the detachment signal conduit 114 is preferably a low voltage direct current electric signal that heats a resistive element 119 and initiates a chain cleavage reaction in the degradable polymer link 115. However, other signals or energy delivery may be used such as alternating or direct electric current, ultrasonic energy, laser energy or any other form of electromagnetic radiation or the like. The detachment signal conduit 114 may be a single, double or multiple pole wire, coaxial cable, fiber optic, elongate ultrasonic energy transmitter, such as a solid rod of metal, glass or composite or the like.

FIG. 22 shows a distal end 121 of a delivery system 122 detachably secured to a first end 123 of a space filling device 124 having features of the invention. The distal end 121 of the delivery system has an elongate tubular shaft 125 with an inner lumen 126 disposed therein. A detachment signal conduit 127 is disposed within the inner lumen 126 of the shaft 125 and is connected to a mechanical capture device 128 at a distal extremity 129 of the conduit. A first extremity 131 of an elongate longitudinal member 132 has an enlarged portion 133 which is mechanically captured by a plurality of capture elements 135 of the mechanical capture device 128. The capture elements 135 can be activated by means of a signal transmitted through the detachment signal conduit 127 which causes the capture elements 135 to expand in an outward radial direction which releases the enlarged portion 133 of the elongated longitudinal member 132 and releases the space filling device 124 from the delivery system 122. The detachment signal transmitted through the detachment signal conduit is preferably a low voltage electrical signal that heats the capture elements 135 which are made of a shape memory alloy such as NiTi and which are configured to have a remembered shape in an open expanded position which results upon heating of the elements. A similar result can be achieved in an alternative embodiment of a mechanical capture device which has capture elements which are radially constrained by an elongated tubular detachment signal conduit. Upon longitudinal retraction of the tubular conduit, the constraint of the capture elements is removed and an enlarged portion released. Alternative detachment signals include alternating or direct electric current, ultrasonic energy, laser energy or any other form of electromagnetic radiation or the like. The detachment signal conduit may be a single, double or multiple pole electrically conducting wire, coaxial cable, fiber optic, elongate tubular member with an inner lumen for conduction of hydrokinetic energy and activation of a hydrokinetic detachment mechanism, elongate ultrasonic energy transmitter, such as a solid rod of metal, glass or composite or the like. The detachment signal may also be in the form of mechanical actuation by longitudinal or rotational translation of a mechanical detachment signal conduit such as an elongate rod, shaft, or tubular member.

FIG. 23 shows a distal end 138 of a delivery system 139 detachably secured to a first end 141 of a space filling device 142 having features of the invention. The distal end 138 of the delivery system has an elongate tubular shaft 143 with an inner lumen 144 disposed therein. A detachment signal conduit 145 is disposed within the inner lumen 144 of the shaft 143 and is connected to a mechanical capture device 146 at a distal extremity 147 of the conduit. A first extremity 148 of an elongate longitudinal member 149 has an enlarged portion 151 which is mechanically captured by a helical capture element 152 of the mechanical capture device 146. The helical capture element 152 can be activated by means of a signal transmitted through the detachment signal conduit 145 which causes the capture element 152 to expand in an outward radial direction which releases the enlarged portion 151 of the elongated longitudinal member 149 and releases the space filling device 142 from the delivery system 139. The detachment signal transmitted through the detachment signal conduit 145 is preferably a low voltage electrical signal that heats the capture element 152 which is made of a shape memory alloy such as NiTi and which is configured to have a remembered shape in an open expanded position which results upon heating of the element. Alternative detachment signals include alternating or direct electric current, ultrasonic energy, laser energy or any other form of electromagnetic radiation or the like. The detachment signal conduit 145 may be a single, double or multiple pole wire, coaxial cable, fiber optic, elongate ultrasonic energy transmitter, such as a solid rod of metal, glass or composite or the like.

An alternative capture element for the mechanical capture device could include a tubular member, preferably in the form of a braided capture element 160 as shown in FIGS. 24-26. The braided capture element 160 as shown is constructed of braided elongated filaments 161 of a shape memory alloy, such as NiTi alloy. The capture element 160 could also be a tubular member of shape memory polymer with similar properties. The elongated filaments 161 are arranged in a braided tubular structure with a first inner diameter 162 which is smaller than a nominal diameter or transverse dimension of an enlarged portion 163, and which mechanically surrounds and captures the enlarged portion. The braided tubular structure of the capture element also has a second remembered inner diameter 171 or transverse dimension which is greater than the transverse dimension of the enlarged portion 163. In this way, the space filling device 168 can be introduced into a desired area of a patient while secured to a distal end 165 of a delivery system 164 by the mechanical pressure of the first inner diameter 162 of the braided capture element 160 on the enlarge portion 163 of the first end 166 of the elongated longitudinal member 167 of the space filling device 168. Upon placement of the space filling device 168 within the desired area within a patient, the shape memory elongated filaments 161 can be activated so as to remember the larger second inner diameter 171 releasing the enlarged portion and the space filling device into the desired area of the patient as indicated by arrow 172. Activation of the braided capture element 160 could be carried out by the application of energy by the various methods described above. Such an embodiment of the capture element as well as any other embodiment of the capture element discussed above, could be used to detach any of the various embodiments of the space filling device discussed herein.

While particular forms of the invention have been illustrated and described, it will be apparent that various modifications can be made without departing from the spirit and scope of the invention. Accordingly, it is not intended that the invention be limited, except as by the appended claims.

What is claimed is:

1. A delivery system for an intracorporeal device comprising:
    an elongated shaft having an inner lumen;
    a degradable link associating the elongated shaft and an intracorporeal device without covering an external circumference of the intracorporeal device, a portion of the degradable link disposed within the inner lumen of the elongated shaft; and
    at least one signal transmission element disposed within the inner lumen of the elongated shaft, the at least one signal transmission element operable to transmit a direct current to initiate degradation of the degradable link thereby completely disassociating the intracorporeal device from the elongated shaft.

2. The delivery system of claim 1, wherein the degradable link comprises a polymeric material.

3. The delivery system of claim 1, wherein the degradable link is degradable by a reaction initiated by heat.

4. The delivery system of claim 1, wherein the at least one signal transmission element is selected from the group consisting of: single pole wire, multiple pole wire, coaxial cable, and fiber optic cable.

5. The delivery system of claim 1, wherein the at least one signal transmission element is in communication with a resistor element, the resistor element disposed proximate to or within the degradable link.

6. The delivery system of claim 5, wherein the at least one signal transmission element communicates an electrical signal to the resistive element.

7. A method for disassociating an intracorporeal device from a delivery system, said method comprising the steps of:
    disposing a portion of a degradable link within an inner lumen of an elongated shaft;
    associating the degradable link to an intracorporeal device without covering an external circumference of the intracorporeal device with the degradable link;
    sending a direct current through at least one electrical conductor disposed within a lumen of the elongated shaft to a resistive heater in operable contact with said degradable link, so as to degrade the degradable link and completely disassociate the intracorporeal device from the elongated shaft.

8. The method of claim 7, wherein the step of sending electricity through at least one electrical conductor comprises sending electricity through a single pole or multiple pole wire.

9. A detachment mechanism for detaching an intracorporeal space-filling device from a delivery system comprising:
- an elongated shaft having an inner lumen;
- a degradable polymer link detachably connecting an intracorporeal device to the elongated shaft wherein at least a portion of the degradable polymer link is disposed within the inner lumen;
- a plurality of wires disposed within said inner lumen of said elongated tubular shaft; and
- a resistive element connected to said plurality of wires, said resistive element operable to degrade the polymer link thereby releasing the intracorporeal device from the elongated tubular shaft.

10. The detachment mechanism of claim 9, wherein a direct current electrical signal causes heat to be generated by said resistive element.

11. A method of occluding an intracorporeal void, said method comprising the steps of:
- positioning the distal end of a microcatheter such that a distal port in the distal end is directed to the cavity of the intracorporeal void;
- deploying a space-filling device into said void wherein said space-filling device is detachably coupled to a delivery system by a polymer link disposed within an inner lumen of said delivery system; and
- detaching said space-filling device from said delivery system by energizing an electric mechanism having wires disposed within the inner lumen of said delivery system.

12. The method of claim 11, wherein the step of detaching said space-filling device comprises energizing said electric mechanism comprises sending electricity to a heating element.

13. The method of claim 12, wherein sending electricity to a heating element comprises sending electricity to a resistive heating element.

* * * * *